(12) United States Patent
Shigeta

(10) Patent No.: US 8,556,803 B2
(45) Date of Patent: Oct. 15, 2013

(54) MEDICAL APPARATUS SYSTEM

(75) Inventor: Ken Shigeta, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 735 days.

(21) Appl. No.: 12/774,826

(22) Filed: May 6, 2010

(65) Prior Publication Data

US 2010/0217075 A1 Aug. 26, 2010

Related U.S. Application Data

(63) Continuation of application No. PCT/JP2008/071414, filed on Nov. 26, 2008.

(30) Foreign Application Priority Data

Dec. 28, 2007 (JP) .................................. 2007-340315

(51) Int. Cl.
*A61B 1/045* (2006.01)
(52) U.S. Cl.
USPC .............. 600/118; 600/145; 600/173; 348/74
(58) Field of Classification Search
USPC ......................................... 600/103, 145, 173
See application file for complete search history.

(56) References Cited

U.S. PATENT DOCUMENTS

| 5,818,527 | A * | 10/1998 | Yamaguchi et al. | 348/335 |
|---|---|---|---|---|
| 6,517,478 | B2 * | 2/2003 | Khadem | 600/117 |
| 7,725,214 | B2 * | 5/2010 | Diolaiti | 700/247 |
| 8,073,528 | B2 * | 12/2011 | Zhao et al. | 600/424 |

| 2003/0163038 | A1 | 8/2003 | Simon et al. | |
|---|---|---|---|---|
| 2004/0059322 | A1 | 3/2004 | Kawai et al. | |
| 2008/0004603 | A1 * | 1/2008 | Larkin et al. | 606/1 |

FOREIGN PATENT DOCUMENTS

| JP | 9-19441 | | 1/1997 | |
|---|---|---|---|---|
| JP | 09019441 | A * | 1/1997 | ............ A61B 19/00 |
| JP | 2001-104333 | | 4/2001 | |
| JP | 2004-89484 | A | 3/2004 | |

(Continued)

OTHER PUBLICATIONS

Shahidi, R et al., "Implementation, Calibration and Accuracy Testing of an Image-Enhanced Endoscopy System", IEEE Transactions on Medical Imaging, IEEE Service Center, Piscataway, NJ, US, vol. 21, No. 12, Dec. 1, 2002, XP011076403.

(Continued)

*Primary Examiner* — Clayton E LaBalle
*Assistant Examiner* — Leon W Rhodes, Jr.
(74) *Attorney, Agent, or Firm* — Scully, Scott, Murphy & Presser, P.C.

(57) ABSTRACT

A medical apparatus system includes: an image generating section that generates an image in an observation field of view obtained from an observing section including an objective lens; an information collecting section that collects information of a treatment instrument; a distortion setting section that sets virtual distortion on the outside of the observation field of view from a characteristic of distortion of the objective lens; a distorted image generating section that generates a distorted image on the outside of the observation field of view with respect to the treatment instrument; and an image combining section that generates a combined image such that an image of the treatment instrument on the inside of the observation field of view and a distorted image of the treatment instrument coincide with each other in a boundary of the observation field of view.

23 Claims, 11 Drawing Sheets

(56) References Cited

FOREIGN PATENT DOCUMENTS

| JP | 2006-227774 A | 8/2006 |
|----|---------------|--------|
| JP | 2007-029232   | 2/2007 |
| JP | 2007-171941   | 7/2007 |
| WO | WO 01/87136 A2 | 11/2001 |

OTHER PUBLICATIONS

Extended Supplementary European Search Report dated Dec. 16, 2010.

* cited by examiner

MEDICAL APPARATUS SYSTEM

CROSS REFERENCE TO RELATED APPLICATION

This application is a continuation application of PCT/JP2008/071414 filed on Nov. 26, 2008 and claims benefit of Japanese Application No. 2007-340315 filed in Japan on Dec. 28, 2007, the entire contents of which are incorporated herein by this reference.

BACKGROUND OF THE INVENTION

1. Field of the Invention

The present invention relates to a medical apparatus system that combines an image on the inside of an observation field of view, in which observing means such as an endoscope is used, and an image including a treatment instrument on the outside of the observation field of view and displays the image.

2. Description of the Related Art

In recent years, an endoscope provided with observing means at a distal end of an elongated insertion portion is widely used in a medical field and the like.

The endoscope is also widely used as a medical apparatus system such as a surgical operation system for performing curative treatment using a treatment instrument under observation by the observing means of the endoscope.

In performing the treatment using the treatment instrument, a surgeon performs the treatment of a diseased part as a treatment target and the distal end of the treatment instrument placed in the observation field of view by the observing means.

In such a case, if the surgeon can recognize a state such as a posture of the treatment instrument on the outside of the observation field of view, the surgeon can easily perform the treatment more smoothly.

For example, in a conventional example of Japanese Patent Application Laid-Open Publication No. 9-19441, in operating a manipulator as a multi joint treatment instrument while looking at an observation image from observing means, it is impossible to grasp the posture of the manipulator on the outside of an observation field of view of the observing means. Therefore, the conventional example discloses an image display apparatus that generates a virtual image of the manipulator on the outside of the observation field of view of the observing means and combines the virtual image with a video actually captured by the observing means.

SUMMARY OF THE INVENTION

A medical apparatus system according to an aspect of the present invention includes:

a medical apparatus including an observing section having an objective lens;

an image generating section on an inside of an observation field of view that generates an image in the observation field of view obtained from the observing section;

an information collecting section that collects information including at least a position on a distal end side of a treatment instrument that can be used together with the medical apparatus;

a distortion setting section that sets virtual distortion on an outside of the observation field of view from a characteristic of distortion of the objective lens;

a distorted image generating section on the outside of the observation field of view that generates at least a three-dimensional or two-dimensional distorted image virtually distorted on the outside of the observation field of view with respect to the treatment instrument on the basis of the information collected by the information collecting section and the virtual distortion; and an image combining section that generates, when the treatment instrument is captured on the inside of the observation field of view, a combined image such that an image of the treatment instrument on the inside of the observation field of view and a distorted image of the treatment instrument on the outside of the observation field of view coincide with each other in a boundary of the observation field of view.

DETAILED DESCRIPTION OF THE PREFERRED EMBODIMENTS

Embodiments of the present invention are explained below with reference to the drawings.

First Embodiment

Figure 1:
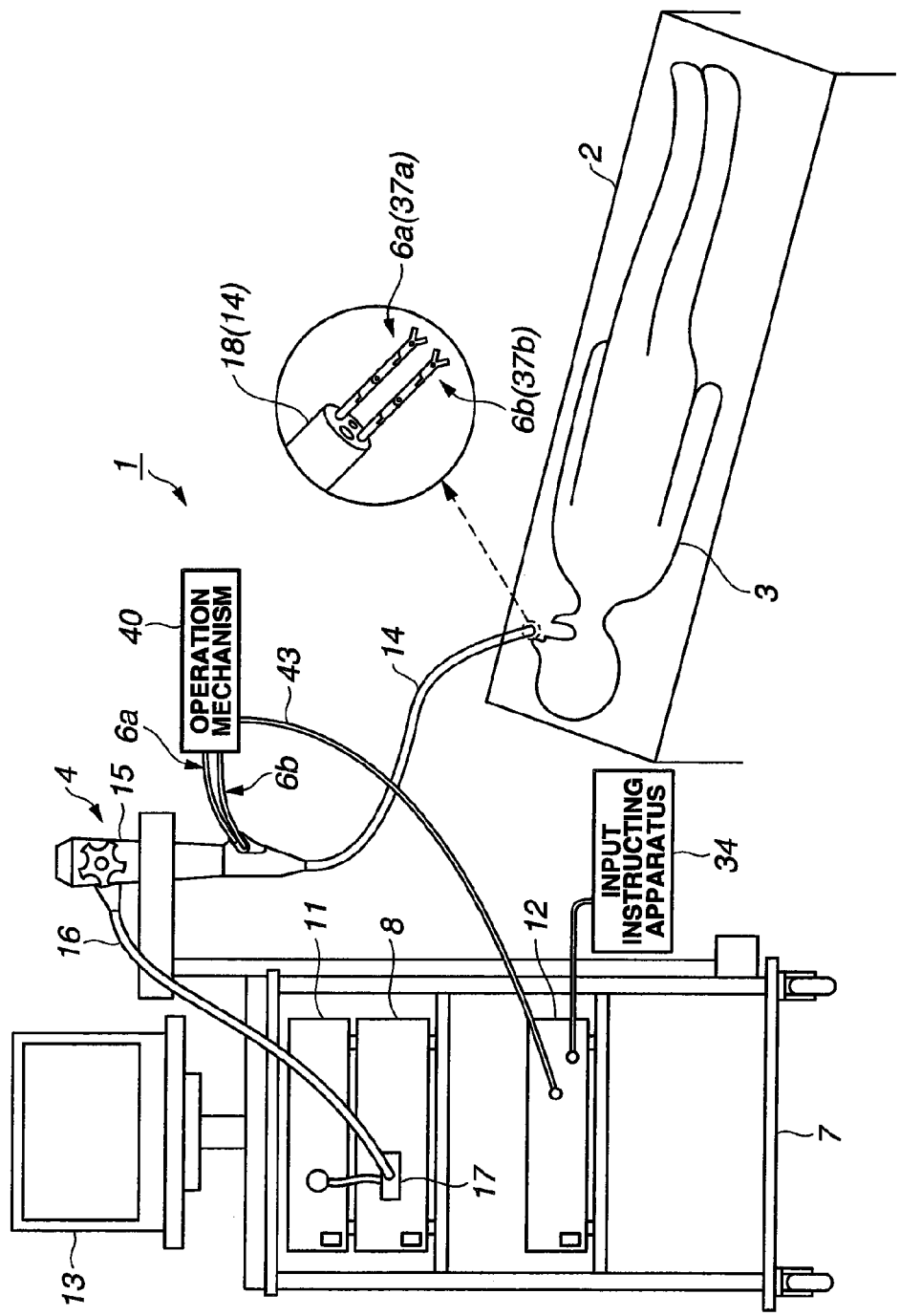
FIG. 1 is a diagram showing an overall configuration of an endoscope system according to a first embodiment as a medical apparatus system according to the present invention.
Figure 2:
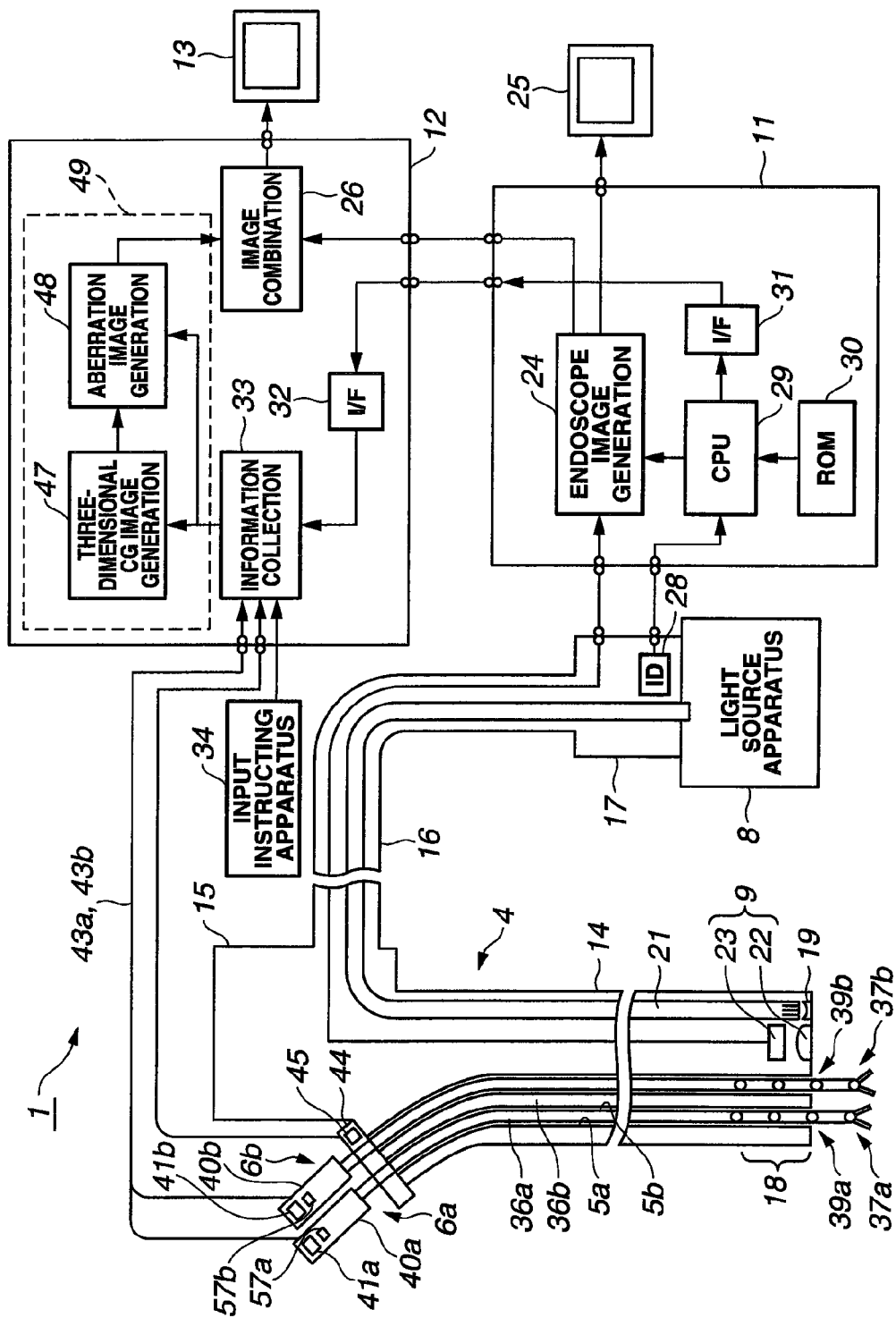
FIG. 2 is a diagram showing an internal configuration in FIG. 1.
Figure 3:
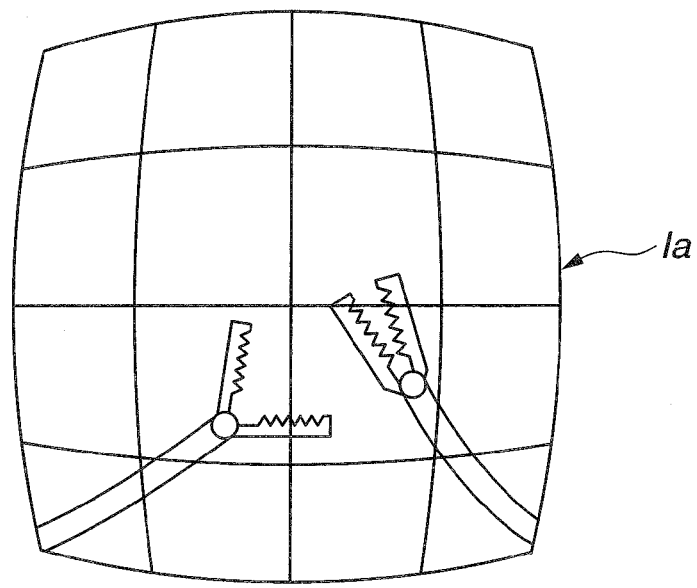
FIG. 3 is a diagram showing an example of an endoscope image as an intra-observation field of view image obtained by a video processor.

FIGS. 1 to 11 relate to a first embodiment of the present invention. FIG. 1 shows an overall configuration of an endoscope system according to the first embodiment as a medical apparatus system according to the present invention. FIG. 2 shows a functional configuration of FIG. 1. FIG. 3 shows an example of an endoscope image as an intra-observation field of view image obtained by a video processor.

Figure 4A:
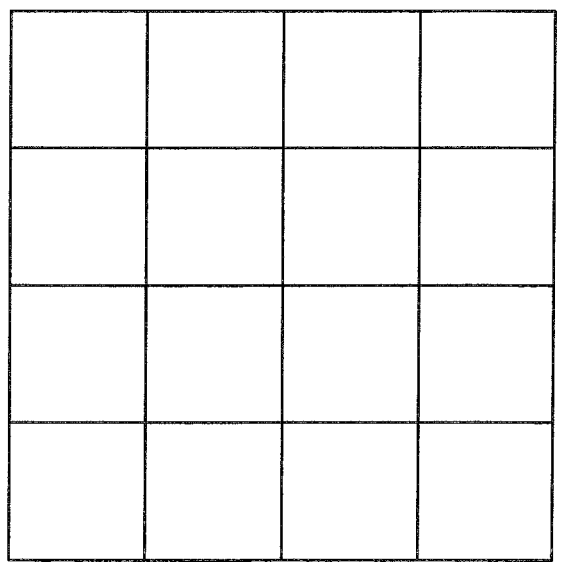
FIG. 4A is a diagram showing an image obtained when a square lattice is formed by an ideal objective lens without distortion.
Figure 4B:
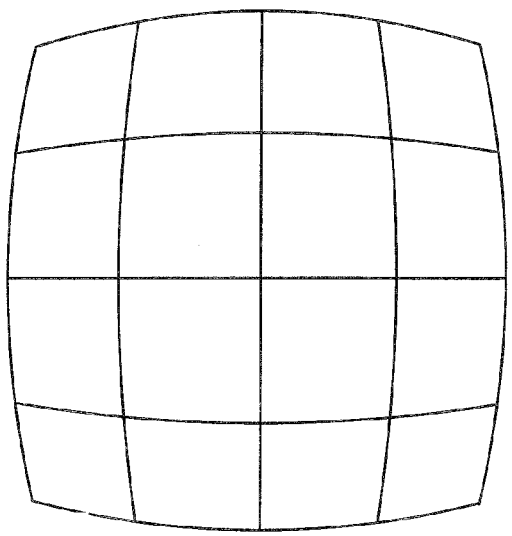
FIG. 4B is a diagram showing an image obtained when the square lattice is formed by an objective lens having distortion.
Figure 5:
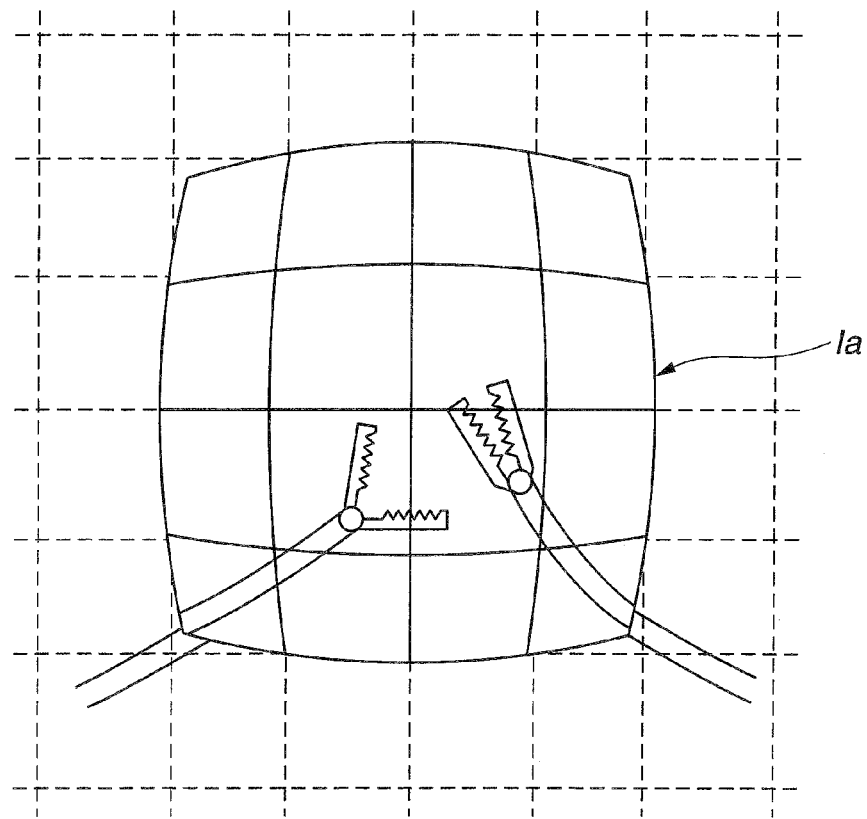
FIG. 5 is a diagram showing an image example obtained when a treatment instrument on the outside of the observation field of view is combined with the treatment instrument on the inside of the observation field of view without distortion applied to the images.

FIG. 4A shows an image obtained when a square lattice is formed by an ideal objective lens without distortion. FIG. 4B shows an image obtained when the square lattice is formed by an objective lens having distortion. FIG. 5 shows an image example obtained when an image of a treatment instrument on the outside of the observation field of view is combined with an image of the treatment instrument on the inside of the observation field of view without distortion applied to the images.

Figure 6:
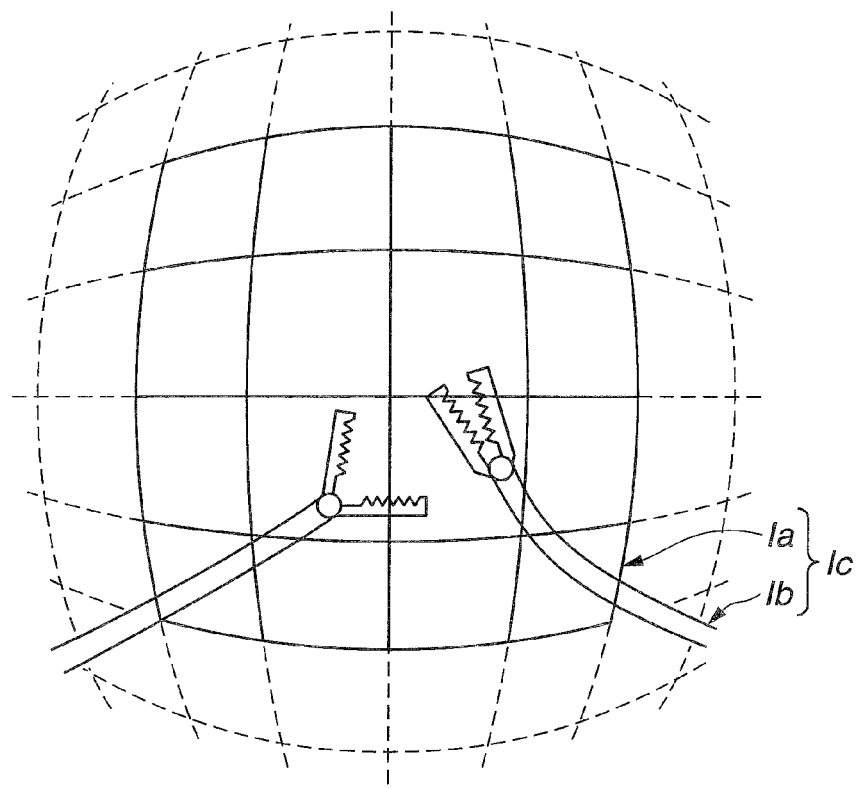
FIG. 6 is a diagram showing an image example obtained when the treatment instrument on the outside of the observation field of view is combined with the treatment instrument on the inside of the observation field of view with distortion applied to the images.
Figure 7:
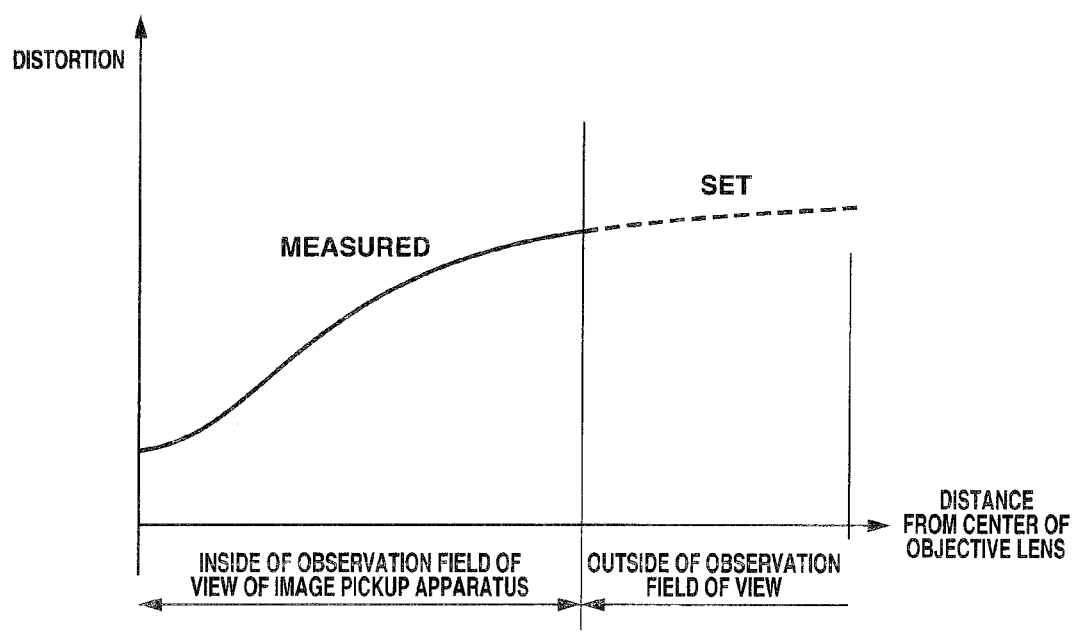
FIG. 7 is a diagram showing a measured characteristic example of distortion on the inside of the observation field of view and a setting example of distortion set on the outside of the observation field of view.
Figure 8:
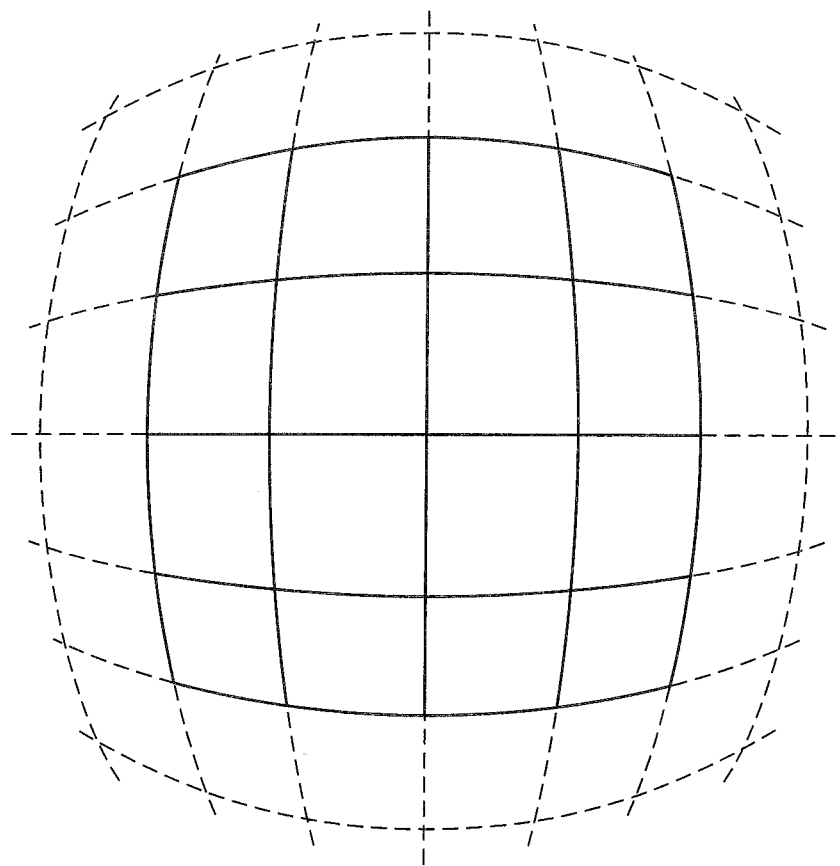
FIG. 8 is a diagram showing an image example in the case in which a square lattice by the distortion set on the outside of the observation field of view set in FIG. 7 is formed.

FIG. 6 shows an image example obtained when an image of the treatment instrument on the outside of the observation field of view is combined with an image of the treatment instrument on the inside of the observation field of view with distortion applied to the images. FIG. 7 shows a measured characteristic example of distortion on the inside of the observation field of view and a setting example of distortion set on the outside of the observation field of view. FIG. 8 shows an image example in the case in which a square lattice by the distortion set on the outside of the observation field of view set in FIG. 7 is formed.

Figure 9:
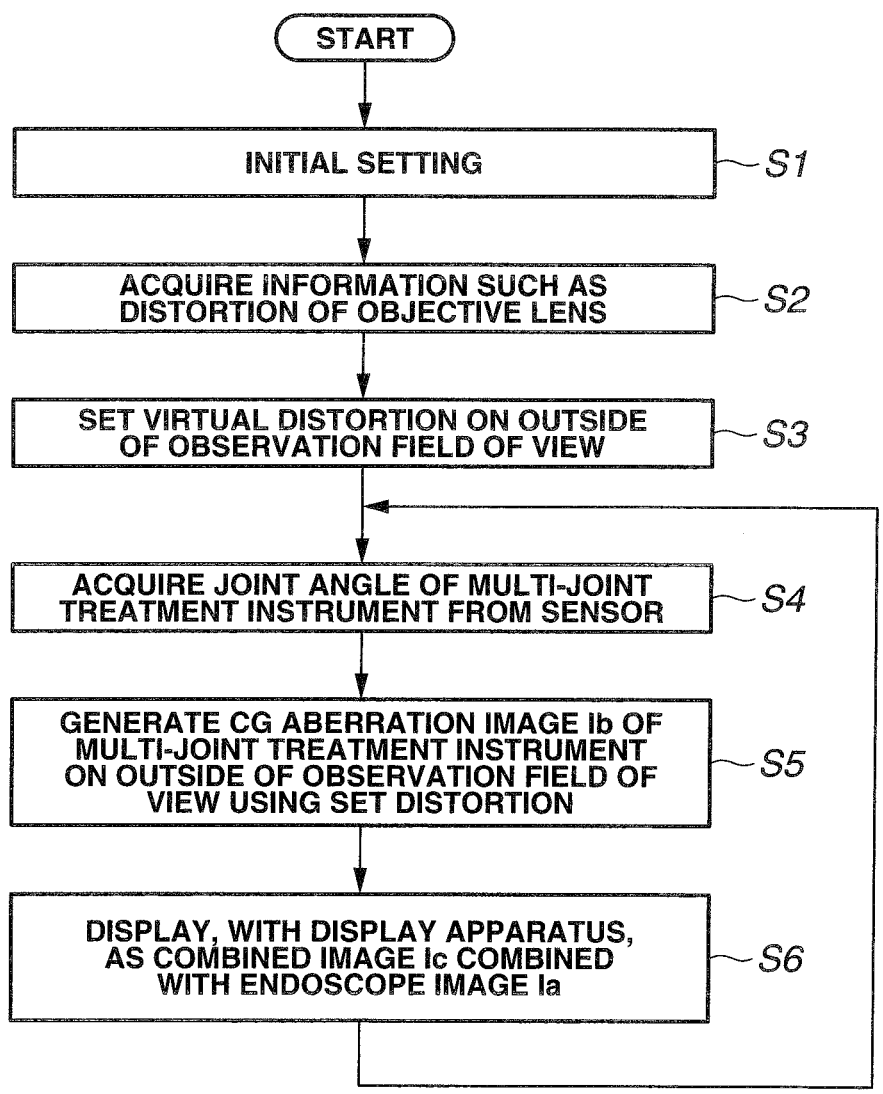
FIG. 9 is a flowchart showing an example of an operation procedure for obtaining a combined image according to the present embodiment.
Figure 10:
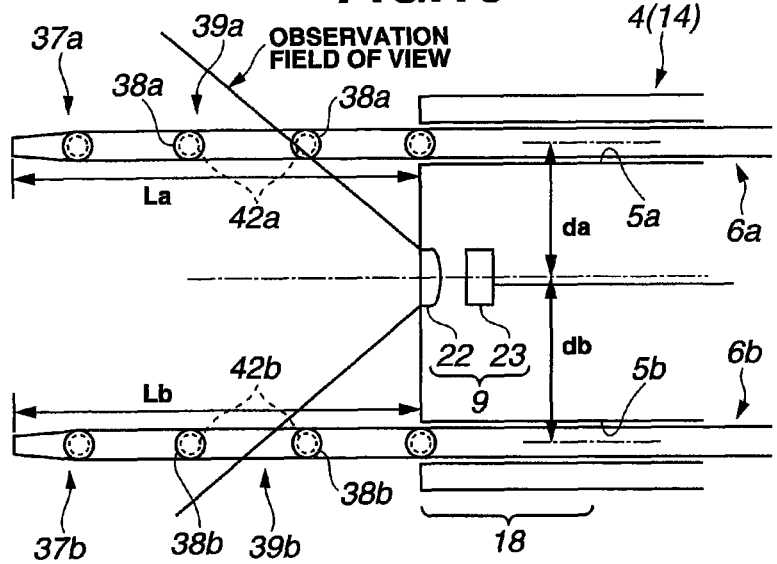
FIG. 10 is a diagram showing a relation between a distal end side of a multi-joint treatment instrument and a distal end side of an endoscope set in initial setting.
Figure 11:
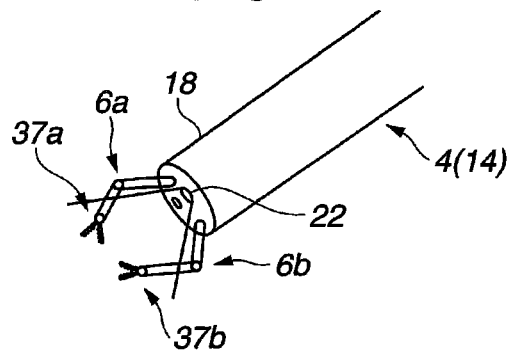
FIG. 11 is a diagram showing an endoscope distal end side in a treatment performing state together with the treatment instrument.

FIG. 9 shows an example of an operation procedure for obtaining a combined image according to the present embodiment. FIG. 10 shows a relation between a distal end side of a multi joint treatment instrument and a distal end side of an endoscope set in initial setting. FIG. 11 shows an endoscope distal end side in a treatment performing state together with the treatment instrument.

As shown in FIG. 1, an endoscope system 1 according to the first embodiment of the present invention includes an endoscope 4 as a medical apparatus for applying inspection and treatment to a patient 3 lying on a bed 2. Channels 5a and 5b (see FIG. 2), through which treatment instruments can be inserted, are provided in the endoscope 4. For example, multi joint treatment instruments 6a and 6b are inserted through the channels 5a and 5b as the treatment instruments.

Medical apparatuses explained below configuring the endoscope system 1 are placed on a cart 7 shown in FIG. 1.

On the cart 7 are placed a light source apparatus 8 that supplies illumination light to the endoscope 4, a video processor 11 that performs signal processing for an image pickup apparatus 9 (see FIG. 2) provided in the endoscope 4 and generates an endoscope image, an image generating apparatus 12 that generates a CG aberration image as an aberration image obtained by applying distortion to a computer graphics image (abbreviated as CG image) as a virtual image on the outside of observation fields of view of the multi joint treatment instruments 6a and 6b and generates a combined image obtained by combining the endoscope image and the CG aberration image, and a display apparatus 13 that displays the combined image.

The endoscope 4 includes a flexible insertion portion 14 that is, for example, elongated and flexible and inserted into a body cavity and the like of the patient 3. An operation portion 15 that a surgeon grips to perform operation such as bending is provided at a rear end of the insertion portion 14. A connector 17 at an end of a universal cord 16 extended out from the operation portion 15 is connected to the light source apparatus 8 and is further detachably connected to the video processor 11, which generates an endoscope image, via a short scope cable.

As shown in FIG. 2, in the endoscope 4, an illumination window and an observation window (an image pickup window) are provided adjacent to each other at a distal end portion 18 of the insertion portion 14. For example, an illumination lens 20 is attached to the illumination window. The endoscope 4 transmits illumination light supplied from the light source apparatus 8 with a light guide 21, further emits the illumination light to an observation target (diagnosis target) region side such as a diseased part in the body cavity via the illumination lens 20, and illuminates the observation target region side.

An optical image of the observation target region illuminated by the illumination light is formed on an image pickup surface of, for example, a charge coupled device (abbreviated as CCD) 23 as a solid-state imaging device, which is arranged in an imaging position of the objective lens 22 attached to the observation window, by the objective lens 22.

The CCD 23 photoelectrically converts the formed optical image and outputs an image pickup signal as a CCD output signal. The image pickup apparatus 9 as observing means for performing observation is composed of the objective lens 22 and the CCD 23.

The image pickup signal is inputted to a picked-up image generating circuit or an endoscope image generating circuit (hereinafter, endoscope image generating circuit) 24 provided in the video processor 11.

The endoscope image generating circuit 24 constituting image generating means on the inside of an observation field of view performs signal processing for the pickup image to thereby generate an image signal (a video signal) for displaying, as an endoscope image Ia, the optical image formed on the image pickup surface of the CCD 23.

The image signal is inputted to, for example, an image combining circuit 26 in the image generating apparatus 12.

The image signal is also outputted to a display apparatus 25 different from the display apparatus 13 shown in FIG. 1. An image by the image signal is displayed as the endoscope image Ia on a display surface of the display apparatus 25.

A display example of the endoscope image Ia is shown in FIG. 3. The endoscope image Ia includes, together with a diseased part region (not shown in FIG. 3) as a treatment target, a part (a distal end side) captured in the observation fields of view in the multi joint treatment instruments 6a and 6b that are arranged near the diseased part region and apply treatment to the diseased part region.

The endoscope image Ia shown in FIG. 3 is equivalent to an image in a state in which respective parts of distal end portions of the multi joint treatment instruments 6a and 6b are captured on the inside of the observation field of view of the objective lens 22, for example, as shown in FIG. 10.

In this case, since the objective lens 22 is required to have an observation field of view with a small size and a wide angle, an optical image formed by the objective lens 22 involves distortion.

The observation field of view in the present embodiment is equivalent to, more strictly, an image pickup area of the image pickup surface of the CCD 23 arranged on the inside of an image-formed range corresponding to a field of view by the objective lens 22. However, for simplification, an expression such as an observation field of view of the objective lens 22 or an observation field of view of the image pickup apparatus 9 is also used.

In the present embodiment, for simplification, it is assumed that a part on a peripheral side of an image formed in the image pickup area of the image pickup surface is directly displayed in a display area of the display apparatus 13 without being masked (it is assumed that the area of the observation field of view and the display area are equivalent). When the part of the peripheral side of the image is masked, the observation field of view or the display area only has to be treated as being narrowed by only a portion cut by the mask.

The influence of the distortion is supplementarily explained with reference to FIGS. 4A and 4B.

When, for example, a square lattice is formed by an objective lens without distortion as a subject, as shown in FIG. 4A, an image similar to the subject is obtained. On the other hand, when the square lattice is formed by the objective lens 22 having distortion, as shown in FIG. 4B, an image of the square lattice distorted in a barrel shape is obtained. In this case, a distortion amount is small in the center portion of the image and is large in a peripheral portion of the image.

Therefore, the endoscope image Ia shown in FIG. 3 changes to the image having the distortion shown in FIG. 4B.

Therefore, a distortion amount of the multi-joint treatment instruments 6a and 6b in the endoscope image is large near the peripheral side of the display area equivalent to the image portion on the peripheral side of the observation field of view.

Consequently, even if a CG image of the multi joint treatment instruments 6a and 6b on the outer side of the display area of the endoscope image Ia is accurately generated (without the distortion due to the objective lens 22 taken into account) and directly combined with the endoscope image Ia by the image generating apparatus 12, the images are not joined such that the multi joint treatment instruments 6a and 6b are continuous, for example, as shown in FIG. 5.

The image shown in FIG. 5 is equivalent to an image obtained by combining a CG image generated by a three-dimensional CG image generating circuit 47 shown in FIG. 2 with the endoscope image Ia using the image combining circuit 26 not through an aberration image generating circuit 48.

To prevent the images from becoming discontinuous as shown in FIG. 5, in the present embodiment, distortion is applied to the CG image as explained below. This makes it possible to generate a combined image in which the CG image is smoothly joined with an image of a treatment instrument in the endoscope image Ia.

By adopting a configuration explained below, even when a type of the endoscope 4 is different, it is possible to generate a combined image Ic shown in FIG. 6.

For example, a connector 17 (which is a portion not separated from each endoscope 4) in the endoscope 4 is mounted with an ID information generating section (simply abbreviated as ID in FIG. 2) 28 that generates ID information as identification information peculiar to the endoscope 4.

The ID information is inputted to a CPU 29 provided in the video processor 11. The CPU 29 is connected to a ROM 30 having stored therein various kinds of information related to the endoscope 4 that generates the ID information. The CPU 29 reads, for example, using the ID information as address information, various kinds of information related to the endoscope 4 corresponding thereto.

The CPU 29 transmits the read various kinds of information to an information collecting section 33 via a communication interface (abbreviated as I/F) 31 and through a communication interface (abbreviated as I/F) 32 in the image generating apparatus 12.

The various kinds of information related to the endoscope 4 stored in the ROM 30 include information concerning a characteristic of the image pickup apparatus 9 mounted on the endoscope 4, more specifically, information concerning a focal distance as an optical characteristic of the objective lens 22 configuring the image pickup apparatus 9, a characteristic of distortion, and characteristic such as the number of pixels, a pixel pitch, and a size of the image pickup surface of the CCD 23, information concerning a specification and a shape characteristic of the endoscope 4, for example, positions of the distal end openings of channels 5a and 5b (of the distal end portion 18) formed in a longitudinal direction of the insertion portion 14, and information concerning a three-dimensional arrangement relation between the positions and the objective lens 22 configuring the image pickup apparatus 9.

For example, the three-dimensional CG image generating circuit 47 that generates a three-dimensional CG image of multi joint treatment instruments 6a and 6b explained later generates a three-dimensional CG of the multi-joint treatment instruments 6a and 6b using the positions of the distal end openings of the channels 5a and 5b as information concerning reference positions.

Specifically, a projection amount of projection from the distal end openings of the channels 5a and 5b of the multi joint treatment instruments 6a and 6b changes and a rotation amount (a rotation angle) in respective joint portions change. However, the projection amount and the rotation amount always change in a state in which the multi joint treatment instruments 6a and 6b pass positions of the distal end openings of the channels 5a and 5b.

Therefore, with the distal end openings of the channels 5a and 5b set as reference positions, in an initial state, initial setting is performed such that postures of the multi joint treatment instruments 6a and 6b can be detected with detection values of sensors 42a and 42b (see FIG. 10) provided in the multi joint treatment instruments 6a and 6b by, for example, straightening up the multi joint treatment instruments 6a and 6b projected from the reference positions (in other words, the detection values of the sensors 42a and 42b are calibrated).

Thereafter, according to detection information of the sensors 42a and 42b provided in the multi joint treatment instruments 6a and 6b, even when the postures of the multi joint treatment instruments 6a and 6b change according to changes in angles (joint angles) of joints 38a and 38b (see FIG. 10) in the multi joint treatment instruments 6a and 6b, the change of the postures can be detected.

Specifically, each sensor 42a provided in each joint portion detects a joint angle at which the multi joint treatment instrument 6a changes according to the rotation in each joint 38a. The plural sensors 42a constitutes detecting means for posture information as information of a posture of the multi joint treatment instrument 6a corresponding to a rotation state of the plural joints 38a. The sensors 42b side also forms detecting means for posture information of the multi joint treatment instrument 6b.

To correspond to the distal end side of the multi joint treatment instruments 6a and 6b in the observation fields of view, for generation of a CG image on the outside of the observation fields of view, information concerning a relative arrangement relation among positions of the distal end openings of the channels 5a and 5b, a center position of the image pickup apparatus 9 as observing means or the objective lens 22, and an observation field of view direction thereof are also necessary.

In the present embodiment, various kinds of information related to each endoscope 4 are collected (by the information collecting section 33) on the basis of ID information peculiar to the endoscope 4. With this configuration, even when a different endoscope 4 is used according to treatment, it is possible to collect various kinds of information required according to the endoscope 4 actually used. Labor and time of the user for manually inputting information can be reduced.

When the information concerning the arrangement relation explained above cannot be acquired from the ID information (e.g., when endoscope information related to the ID information does not include information concerning a three-dimensional detailed arrangement relation among positions of the distal end openings of the channels 5a and 5b, a position of the image pickup apparatus 9, and a field of view direction) or when the information cannot be obtained at required accuracy, the user can also input the information from an input instructing apparatus 34 to the information collecting section 33 as explained later.

The present embodiment is explained in the case of the multi joint treatment instruments 6a and 6b. However, even when the multi joint treatment instruments 6a and 6b are changed, this embodiment can also be applied to the changed treatment instruments.

In FIG. 2, the information collecting section 33 collects the ID information via the video processor 11. However, the information collecting section 33 may directly collect various kinds of information related to the endoscope 4 from the ID information.

The information collecting section 33 is connected to the input instructing apparatus 34. The user like a surgeon can input information necessary for, for example, generation of a CG image from the input instructing apparatus 34. For example, the user can input relative position information among the distal end openings of the channels on the distal end surface of the insertion portion 14, a center position of the objective lens 22, and a field of view direction thereof.

Information concerning a direction in which the multi joint treatment instruments 6a and 6b are projected from the distal end openings of the channels is also inputted from the input instructing apparatus 34 to the information collecting section 33. The information collecting section 33 may automatically collect this direction information according to the ID information of the endoscope 4. This information is information that usually does not temporally change unlike posture information explained below.

In other words, the information collecting section 33 collects, in order to generate a CG aberration image obtained by distorting a CG image, position information of a relative arrangement relation between the multi joint treatment instruments 6a and 6b and the observing means (the image pickup apparatus 9) of the distal end portion 18 of the endoscope 4 for generating the endoscope image Ia, direction information, and posture information.

For example, position information, direction information, and posture information for deciding postures of the multi joint treatment instruments 6a and 6b in the state of the initial setting can be inputted.

In the case of an endoscope in which the ID information generating section 28 is not provided or required various kinds of information cannot be sufficiently decided, the required various kinds of information can be inputted from the input instructing apparatus 34.

The multi joint treatment instruments 6a and 6b as treatment instruments inserted into the channels 5a and 5b have elongated flexible portions 36a and 36b. A treatment section 37i that performs various kinds of treatment is formed at a distal end portion of the flexible portion 36i (i=a and b).

A manipulator section 39i is formed by plural joints 38i near a rear end of the treatment section 37i, i.e., a distal end side in the flexible portion 36i. The surgeon can drive the manipulator section 39i to change postures on the distal end side of the multi joint treatment instruments 6a and 6b and perform various kinds of treatment by operating an operation mechanism 40i (in FIG. 1, one operation mechanism 40 is shown in a simplified form).

A control section 41i that drives a motor of each joint 38i forming the manipulator section 39i is provided in the operation mechanism 40i.

A rotation amount of each joint 38i driven to rotate by the motor is detected by a sensor 42i such as a rotary encoder attached to a rotating shaft. A detection signal of each sensor 42i is inputted to the information collecting section 33 via a cable 43i (in FIG. 1, indicated by one cable 43). The same can be applied to a treatment instrument having structure in which the joints 38a and 38b can be manually driven without the motor.

As shown in FIG. 2, a treatment instrument holder 44 is attached to treatment instrument insertion ports at rear ends of the channels 5a and 5b. The treatment instrument holder 44 is provided with a movement amount detection sensor that slidably comes into contact with outer circumferential surfaces of the flexible portions 36a and 36b and detects movement in an axis direction thereof and a rotation amount sensor that detects a rotation amount around a shaft.

A detection signal by a sensor section 45 including a movement amount detection sensor and a rotation amount detection sensor is also inputted to the information collecting section 33.

For example, in a certain state such as the initial setting, a position in a longitudinal direction (an axis direction) on an operator's side and a rotation amount corresponding to a projection amount on the distal end side of the multi joint treatment instruments 6a and 6b projected from the distal end openings of the channels 5a and 5b are set to a movement amount and a rotation amount as reference values. This makes it possible to detect a position and a rotation position on the distal end side of the multi joint treatment instruments 6a and 6b located in the distal end openings of the channels 5a and 5b from a movement amount and a rotation amount detected on the operator's side afterwards.

This also makes it possible to detect a position and a rotation position on the distal end side of the multi joint treatment instruments 6a and 6b projected from the distal end openings of the channels 5a and 5b.

Therefore, the movement amount detection sensor calculates information concerning positions of the multi joint treatment instruments 6a and 6b (i.e., position information). Since the channels 5a and 5b have fixed length, when a position on the operator's side is detected, a position on the distal end side can also be detected.

Supplementarily explaining the above, for example, when the entire multi-joint treatment instrument 6a is rotated in a longitudinal direction thereof, a posture in only the multi joint treatment instrument 6a does not change but the distal end side of the multi joint treatment instrument 6a viewed from the image pickup apparatus 9 changes. However, since detection information by only the sensor 42i provided in the multi joint treatment instrument 6a does not change, the change on the distal end side cannot be detected. The change is detected by the rotation amount detection sensor.

In the present embodiment, a sensor outputted by the rotation amount detection sensor is also used to generate a CG aberration image on the outside of the observation fields of view of the multi joint treatment instruments 6a and 6b to keep a relation with the multi joint treatment instruments 6a and 6b in the observation field of view by the image pickup apparatus 9. When the multi joint treatment instruments 6a and 6b are moved as a whole, the movement amount detection sensor detects a movement amount thereof that cannot be detected by the sensor 42i.

A position detection sensor including a coil for magnetic field generation that can detect a three-dimensional position may be provided on the distal end side to make the movement amount detection sensor unnecessary. Plural coils for magnetic field generation or the like may be provided to make the rotation amount detection sensor unnecessary.

For example, at least one coil for magnetic field generation may be provided for each joint to detect posture information of the multi-joint treatment instruments 6a and 6b. Postures including states of the joints of the multi joint treatment instruments 6a and 6b can also be detected by plural position detecting means.

A direction of the multi joint treatment instruments 6a and 6b can also be detected by the plural position detecting means. The multi joint treatment instruments 6a and 6b having the plural joints are explained above. However, the same can be applied to a treatment instrument having one joint.

The information such as the posture information, the position information, and the direction information collected by the information collecting section 33 is inputted to the three-dimensional CG image generating circuit 47 that generates a three-dimensional CG of the multi joint treatment instruments 6a and 6b and the aberration image generating circuit 48 that generates a CG aberration image Ib as an aberration image thereof.

In FIG. 2, the three-dimensional CG image generating circuit 47 and the aberration image generating circuit 48 are divided. However, the three-dimensional CG image generating circuit 47 and the aberration image generating circuit 48 may be an aberration image generating section 49 as distortion generating means on the outside of an observation field of view formed by integrating both the circuits.

The aberration image generating section 49 may include the function of the image combining circuit 26. The three-dimensional CG image generating circuit 47 can basically generate a three-dimensional CG image of the multi joint treatment instruments 6a and 6b only with information concerning the multi joint treatment instruments 6a and 6b except a point concerning a range of an observation field of view.

In the present embodiment, to generate a three-dimensional CG image of the multi joint treatment instruments 6a and 6b on the outer side of the observation field of view of the endoscope 4, the three-dimensional CG image generating circuit 47 generates a three-dimensional CG image by also using information on the endoscope 4 side collected by the information collecting section 33.

Similarly, the aberration image generating circuit 48 generates a three-dimensional CG aberration image as an aberration image subjected to distortion that is smoothly joined with the characteristic of the distortion of the objective lens 22 in the boundary of the observation field of view with respect to the three-dimensional CG image of the multi joint treatment instruments 6a and 6b are generated by the three-dimensional CG image generating circuit 47.

The aberration image generating circuit 48 converts the three-dimensional CG aberration image into a two-dimensional CG aberration image Ib viewed from an observation field of view direction of the objective lens 22 and outputs the two-dimensional CG aberration image Ib to the image combining circuit 26. The image combining circuit 26 can combine the two-dimensional CG aberration image Ib with the endoscope image Ia to generate a combined image Ic shown in FIG. 6.

The aberration image generating circuit 48 may generate the two-dimensional CG aberration image Ib viewed from the observation field of view direction of the objective lens 22 with respect to the three-dimensional CG image of the multi joint treatment instruments 6a and 6b. In this case, the aberration image generating circuit 48 outputs the CG aberration image Ib to the image combining circuit 26.

The image combining circuit 26 performs image combination to generate the combined image Ic using the endoscope image Ia on the inside of the observation field of view and using the CG aberration image Ib on the outside of the observation field of view.

In this case, when the aberration image generating circuit 48 generates a CG aberration image including a part of the observation field of view in advance and outputs the CG aberration image to the image combining circuit 26, the aberration image generating circuit 48 may delete a portion of the CG aberration image Ib on the inside of the observation field of view or set the portion to a black level and add or embed the endoscope image Ia in the deleted portion of the CG aberration image Ib on the inside of the observation field of view or the black level portion to generate the combined image Ic.

FIG. 7 shows a characteristic example of distortion of the objective lens 22. As shown in FIG. 7, a value of the distortion of the objective lens 22 is the smallest in the center thereof and increases as a distance from the center increases.

Therefore, the value of the distortion is the largest in the boundary portion of the observation field of view. The characteristic of the distortion of the objective lens 22 is measured in advance. Information concerning the characteristic is stored in storing means or the like.

In the present embodiment, the information concerning the characteristic of the distortion of the objective lens 22 mounted on each endoscope 4 is stored in the ROM 30 in advance. When the CG aberration image Ib is generated, the information is used.

In this case, since the information concerning the distortion is not actually present on the outer side of the observation field of view, a characteristic of virtual distortion on the outside of the observation field of view is set from a characteristic of the distortion on the inside of the observation field of view. More specifically, when an aberration image on the outside of the observation field of view is generated, at least in the boundary of the observation field of view, a value of distortion in the boundary of the observation field of view of the objective lens 22 is used. Further, on the outer side than the boundary, a set value of distortion that is smoothly joined with the value of the distortion in the boundary is used.

For example, in the boundary of the observation field of view of the objective lens 22, a straight line (a line segment) as extension of a tangent of distortion in a position of the boundary is used as a characteristic to which distortion for generating the CG aberration image Ib is applied. The setting of the characteristic is automatically performed by, for example, the CPU 29 from the characteristic of the distortion of the objective lens 22 stored in the ROM 30. In other words, the CPU 29 configures distortion setting means for performing setting of virtual distortion.

The setting of the distortion is not limited to such automatic setting. The user may set the characteristic with a keyboard, other input means, or the like from the characteristic of the distortion of the objective lens 22. Information concerning the set virtual distortion is transmitted to the information collecting section 33 and sent from the information collecting section 33 to the aberration image generating circuit 48. The CG aberration image Ib is generated by the aberration image generating circuit 48 using the information.

FIG. 8 shows, with a dotted line, an example in which the distortion is applied to an image of a square lattice by using the characteristic setting of the distortion on the outside of the observation field of view set in this way. A solid line indicates an image on the inside of the observation field of view by the objective lens 22 side. The outside of the observation field of view indicates an image portion to which the virtually set distortion is applied.

As explained above, the distortion is set to the characteristic that is smoothly joined with the distortion portion in the boundary of the observation field of view of the objective lens 22.

The aberration image generating circuit 48 converts the generated three-dimensional CG aberration image into the two-dimensional CG aberration image Ib viewed from the observation field of view direction of the image pickup apparatus 9 of the endoscope 4 and outputs the two-dimensional CG aberration image Ib to the image combining circuit 26.

The image combining circuit 26 combines the endoscope image Ia outputted from the video processor 11 and the two-dimensional CG aberration image Ib of the multi joint treatment instruments 6a and 6b outputted from the aberration image generating circuit 48 to generate the combined image Ic and outputs (an image signal of) the combined image to the display apparatus 13. The combined image Ic of the endoscope image Ia as an intra-observation field of view image and the two-dimensional CG aberration image Ib of the multi joint treatment instruments 6a and 6b as the observation field of view image is displayed on the display apparatus 13.

The operation according to the present embodiment is explained below with reference to a flowchart of FIG. 9.

First, the endoscope system 1 is set as shown in FIG. 1 or 2. Specifically, the surgeon connects the endoscope 4 to be used to the light source apparatus 8 and the video processor 11, inserts the multi joint treatment instruments 6a and 6b into the channels 5a and 5b of the endoscope 4, and connects operation mechanisms 40a and 40b (40) of the multi joint treatment instruments 6a and 6b to the image generating apparatus 12. The surgeon turns on a power supply for the apparatuses and sets the apparatuses in an operation state.

The surgeon performs initial setting in step S1. For example, first, the surgeon sets the multi joint treatment instruments 6a and 6b inserted in the channels 5a and 5b in a straight state. The surgeon inputs information necessary for generation of the CG aberration image Ib in that case to the information collecting section 33 from the input instructing apparatus 34, for example, manually.

FIG. 10 shows the objective lens 22 on the distal end side of the endoscope 4 and the distal end side of the multi joint treatment instruments 6a and 6b inserted in the channels 5a and 5b in the state of the initial setting.

Information concerning projection amounts 1a and 1b of the multi joint treatment instruments 6a and 6b projected from the distal end openings of the channels 5a and 5b as shown in FIG. 10 is inputted. An initial value of a rotation angle around the shaft of the multi joint treatment instruments 6a and 6b is inputted.

Values of distances da and db between the center axis of the objective lens 22 and the centers of the channels 5a and 5b (although planarly shown in FIG. 10, actually, besides the distances da and db, information concerning directions of the distances) are acquired in the information collecting section 33 by manual input or the like by the user.

As shown in step S2, the information collecting section 33 acquires information concerning the distortion of the objective lens 22, information concerning a range of an observation field of view, and the like.

As shown in step S3, the user sets virtual distortion on the outside of the observation field of view. Concerning the setting, the user sets the virtual distortion as explained with reference to FIGS. 7 and 8. The user resets values of the sensors 42a, 42b, and the like and sets the values to specified values.

First, after performing calibration such that correct values can be obtained as values of the sensors, as shown in step S4, the sensors 42a and 42b accurately acquire joint angels of the multi joint treatment instruments 6a and 6b according to movement of the multi joint treatment instruments 6a and 6b.

As shown in the next step S5, the aberration image generating section 49 generates the CG aberration image Ib of the multi joint treatment instruments 6a and 6b on the outside of the observation field of view according to, for example, information concerning the joint angles of the multi joint treatment instruments 6a and 6b from the sensors 42a and 42b.

In the next step S6, the CG aberration image Ib is combined with the endoscope image Ia on the inside of the observation field of view and displayed on the display apparatus 13 as the combined image Ic.

For example, when the endoscope 4 and the multi joint treatment instruments 6a and 6b are set in a state shown in FIG. 11, an image is displayed on the display apparatus 13 as shown in FIG. 6. Specifically, images of the multi joint treatment instruments in the endoscope image Ia on the inside of the observation field of view and the CG aberration image Ib of the multi joint treatment instruments 6a and 6b on the outside of the observation filed of view are displayed as the combined image Ic in which the images are smoothly joined in the boundary of the observation field of view.

When the processing in step S6 is performed, the operation returns to the processing in step S4. When the surgeon moves the multi joint treatment instruments 6a and 6b for treatment, joint angles in that case are acquired by the sensors 42a and 42b. The processing in steps S4 to S6 is repeated.

Besides, when the multi joint treatment instruments 6a and 6b are projected in the axis direction or rotated around the shaft, a state of the combined image Ic in which the endoscope image Ia and the CG aberration image Ib are continuously joined as shown in FIG. 6 is maintained.

In this way, according to the present embodiment, a combined image in which the treatment instruments in both the images on the inside of the observation field of view and on the outside of the observation field of view are continuous can be generated. Therefore, the surgeon can grasp a state of the treatment instruments on the outside of the observation field of view in an easily visible (natural) state and can more smoothly perform curative treatment by Endoscopic Submucosal Dissection (ESD) or the like.

In the present embodiment, the information collecting section 33 can correct, according to the ID information of the endoscope 4, information concerning an optical characteristic and the like including the distortion of the objective lens 22 used in the image pickup apparatus 9 used in the endoscope 4 corresponding to the ID information and use the information to generate the CG aberration image Ib.

Therefore, it is possible to reduce labor and time of manual information input and, even when the endoscope 4 is different, generate a combined image in which treatment instruments in both images on the inside of an observation field of view and on the outside of the observation field of view are continuous.

ID information generating sections (see reference signs 57a and 57b in FIG. 2) that generate ID information for treatment instruments may be provided in treatment instruments inserted into the channels 5a and 5b of the endoscope 4 to make it possible to generate, from the ID information, a three-dimensional CG image of the treatment instruments corresponding to the ID information and the CG aberration image Ib of the treatment instruments, for example, in the image generating apparatus 12.

Consequently, even when the treatment instruments used for treatment are changed together with the endoscope 4, in the case of the treatment instruments, a combined image in which the treatment instruments in both images on the inside of the observation field of view and on the outside of the observation field of view are continuous can be generated.

According to the present embodiment, a combined image in which the treatment instruments in both the images on the inside of the observation field of view and the outside of the observation field of view are continuous can be generated. The surgeon can perform, by referring to the combined image, treatment by the treatment instruments in an environment in which the treatment can be easily performed.

Second Embodiment

A second embodiment of the present invention is explained below with reference to FIG. 12. In the explanation of the first embodiment, when the multi-joint treatment instruments 6a and 6b pass the predetermined position on the distal end surface of the insertion portion 14, postures of the multi joint treatment instruments 6a and 6b change.

On the other hand, an endoscope system according to the present embodiment can be applied to an endoscope 4B in which distal end openings 53a and 53b of the tubes for treatment instrument insertion (hereinafter simply referred to as tubes) 50a and 50b, i.e., outlets of the multi joint treatment instruments 6a and 6b are provided nearer to a proximal side than, for example, two bending portions 51 and 52 formed on the rear end side of the distal end portion 18 in the insertion portion 14.

In this case, besides the postures of the multi joint treatment instruments 6a and 6b, information concerning relative position and posture relations between the distal end openings 53a and 53b of the tubes 50a and 50b and the image pickup apparatus 9 is necessary.

In the endoscope 4B, the image pickup apparatus 9 is provided at the distal end portion 18 of the insertion portion 14. The first bending portion 51 is provided in a rear end portion of the distal end portion 18 and the second bending portion 52 is provided in a portion on a rear side from the rear end portion by predetermined length.

The distal end openings 53a and 53b of the tubes 50a and 50b are provided near a rear end of the second bending portion 52.

The bending portions 51 and 52 are driven to bend by being tugged from an operator's side, for example, the operation portion 15 side shown in FIG. 2 via a wire inserted through the insertion portion 14. A rear end side of the wire inserted through the insertion portion 14 is formed, for example, as shown in FIG. 12. For example, rear ends of a pair of wires 54a and 54b corresponding to driving for bending in an up-to-down direction are laid over, for example, a pulley 55.

The pulley 55 is rotated by bending operation, whereby one of the wires 54a and 54b is tugged. An amount of the tug is detected by an encoder 56. A detection signal of the encoder 56 is inputted to the information collecting section 33 shown in FIG. 2.

Figure 12:
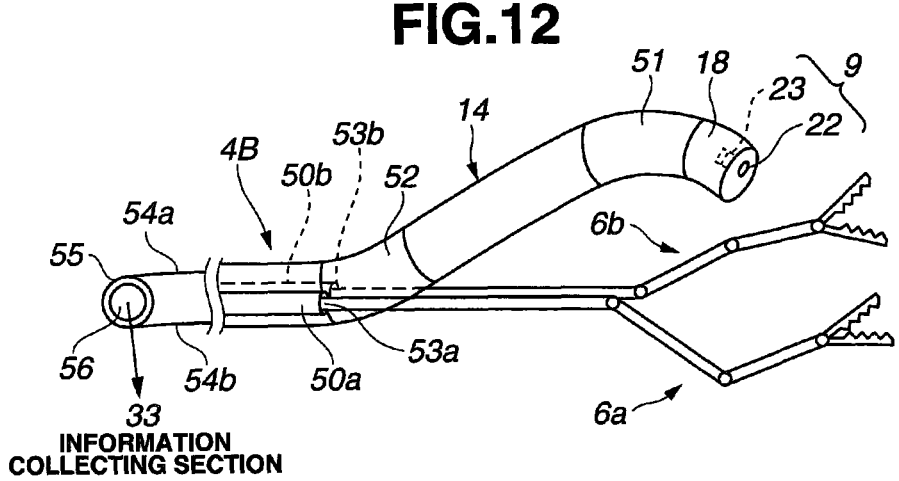
FIG. 12 is a diagram showing a part of an endoscope and a multi joint treatment instrument according to a second embodiment of the present invention.

In the example shown in FIG. 12, for example, only a bend detecting mechanism in an up-to-down direction in the first bending portion 51 is shown. However, a bend detecting mechanism in a left-to-right direction is also provided. The bend detecting mechanism for the second bending portion 52 has the same configuration as that for the first bending portion 51.

In this way, information concerning bending of the bending portions 51 and 52 can be acquired according to detection signals of plural encoders 56. A three-dimensional position and a field of view direction of the image pickup apparatus 9 at the distal end portion 18 of the endoscope 4B can be calculated according to the detection signals of the plural encoders 56.

For example, a position detecting sensor or the like may be attached to the distal end portion 18 to make it possible to calculate a three-dimensional position thereof such that the calculation of the three-dimensional position and the field of view direction of the image pickup apparatus 9 can be more accurately detected. A position detecting apparatus or an insertion shape detecting apparatus may be used in which plural source coils that generate magnetism in the axis direction of the insertion portion 14 are arranged and a sense coil unit including plural sense coils that detect three-dimensional positions of the source coils is arranged, for example, around the bed 2.

The multi joint treatment instruments 6a and 6b are movable, via the cylindrical tubes 50a and 50b fixed to an outer circumferential surface of the insertion portion 14 (by, for example, a tape), from the distal end openings 53a and 53b of the tubes 50a and 50b.

The tubes 50a and 50b are fixed to the insertion portion 14. Information concerning relative position and posture relations between the distal end openings 53a and 53b and the image pickup apparatus 9 is obtained.

The other components are substantially the same as those in the first embodiment. In the present embodiment, as in the first embodiment, a combined image in which treatment instruments in both images on the inside of an observation field of view and on the outside of the observation field of view are continuous can be generated.

The encoder 56 can be replaced with other kinds of position sensors and angle sensors such as a potentiometer. Instead of measuring an amount of tug of wires such as the wires 54a and 54b with the encoder 56, it is also possible to attach a distortion gauge to the bending portions 51 and 52 and measure (detect) a bending angle with the distortion gauge.

In the present embodiment, in substantially the same manner as in the first embodiment, a combined image in which treatment instruments in both images on the inside of an observation field of view and on the outside of the observation field of view are continuous can be generated. A surgeon can easily perform treatment more smoothly.

Third Embodiment

Figure 13:
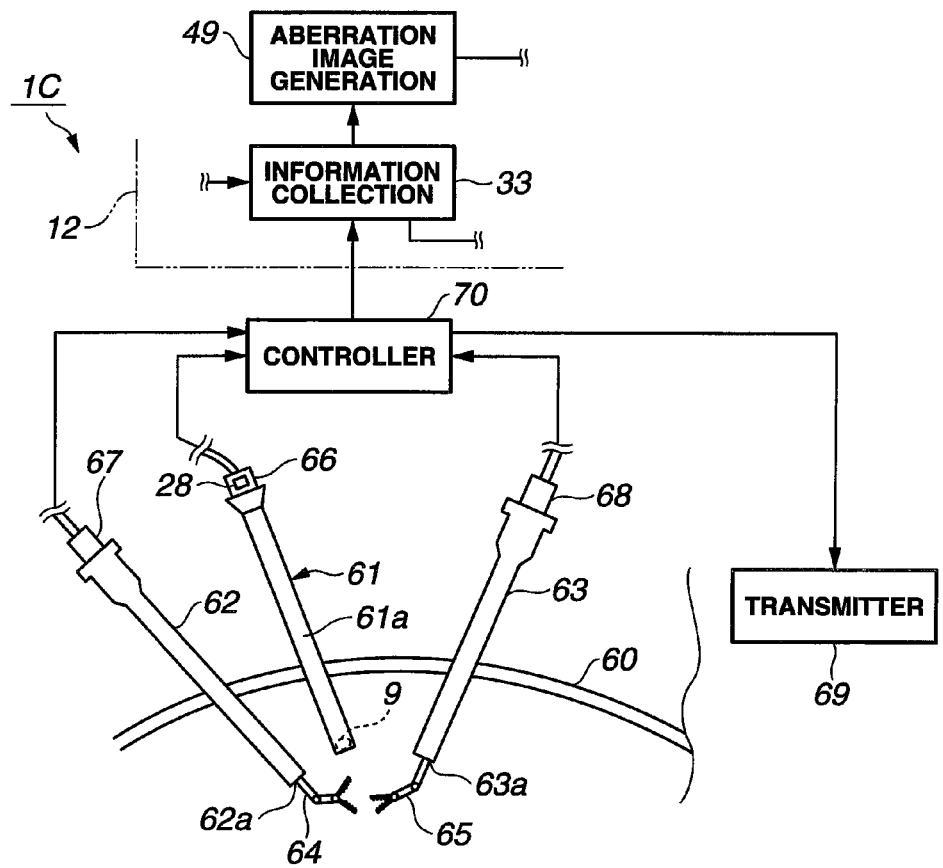
FIG. 13 is a diagram showing a part of an endoscope system including an endoscope and a multi joint treatment instrument used separately from the endoscope according to a third embodiment of the present invention.

A third embodiment of the present invention is explained below with reference to FIG. 13. In the explanations of the first and second embodiments, the multi joint treatment instruments 6a and 6b are used in the endoscopes 4 and 4B in a nearly integral state. On the other hand, in a case such as laparoscope operation, an endoscope and a treatment instrument are often separately used. The present embodiment can also be applied to such a case.

In this case, as in the first and second embodiments, information concerning relative position and posture relations between the image pickup apparatus 9 and an outlet of the treatment instrument can be acquired to make it possible to cope with the case in which the endoscope and the treatment instrument are separately used. FIG. 13 shows a configuration of a part of an endoscope system 1C according to the third embodiment.

A rigid endoscope 61 inserted into an abdominal cavity 60 of a patient includes a rigid insertion portion 61*a*. The image pickup apparatus 9 (including a not-shown objective lens and a not-shown CCD) is provided at a distal end of the insertion portion 61*a*. The rigid endoscope 61 also includes the ID information generating section 28 that generates ID information peculiar thereto.

Two treatment instrument guides 62 and 63 include rigid guide tubes that lead the treatment instruments 64 and 65 from the outside of the body of the patient to a diseased part in the abdominal cavity 60.

For example, a receiver 66 is attached to a rear end of the rigid endoscope 61 and receivers 67 and 68 are respectively attached to the treatment instruments 64 and 65 near rear ends of the treatment instrument guides 62 and 63.

The receivers 66, 67, and 68, a transmitter 69, and a controller 70 configure a position and posture detecting system that measures (detects) positions and postures of the receivers 66, 67, and 68 with magnetism.

For example, the transmitter 69 arranged in a predetermined position generates (transmits) a magnetic field. The receivers 66, 67, and 68 can respectively calculate three-dimensional positions of the receivers 66, 67, and 68 and directions around axes thereof by detecting (receiving) the magnetic field.

The receiver 66 (and the receivers 67 and 68) can also detect directions besides positions because of a configuration including plural sensors.

When the treatment instruments 64 and 65 have joints, as explained in the first embodiment, detection angles of sensors provided in the joints are transmitted to the controller 70.

Information including positions and postures detected by the receivers 66, 67, and 68 is transmitted to the controller 70. The controller 70 calculates, for example, with arithmetic operation, positions and postures of the respective receivers 66, 67, and 68 on the basis of the information transmitted from the receivers 66, 67, and 68 and the like. In other words, the controller 70 forms position and posture detecting means.

Further, the controller 70 calculates, from a calculated result, a relative positional relation between the image pickup apparatus 9 and (guide tube) outlets 62*a* and 63*a* of the treatment instrument guides 62 and 63 in the treatment instruments 64 and 65.

The controller 70 transmits information concerning the calculated positional relation to the information collecting section 33 in the image generating apparatus 12. The aberration image generating section 49 generates the CG aberration image Ib as explained in the first embodiment according to the information collected by the information collecting section 33.

As in the first embodiment, a combined image in which treatment instruments in both images on the inside of an observation field of view and on the outside of the observation field of view are continuous can be generated. Otherwise, this embodiment is the same as the first embodiment. An endoscope system that can cope with both the case can be configured by combining the present embodiment and the first embodiment.

In the explanation of the embodiment, the treatment instrument includes one or more joints. However, the present invention is not limited to this case and can also be applied to a treatment instrument not having a joint.

Figure 14:
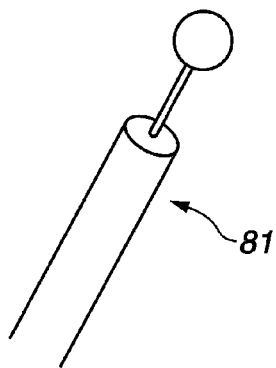
FIG. 14 is a diagram showing an IT knife as a treatment instrument not having a joint usable in the present invention.
Figure 15:
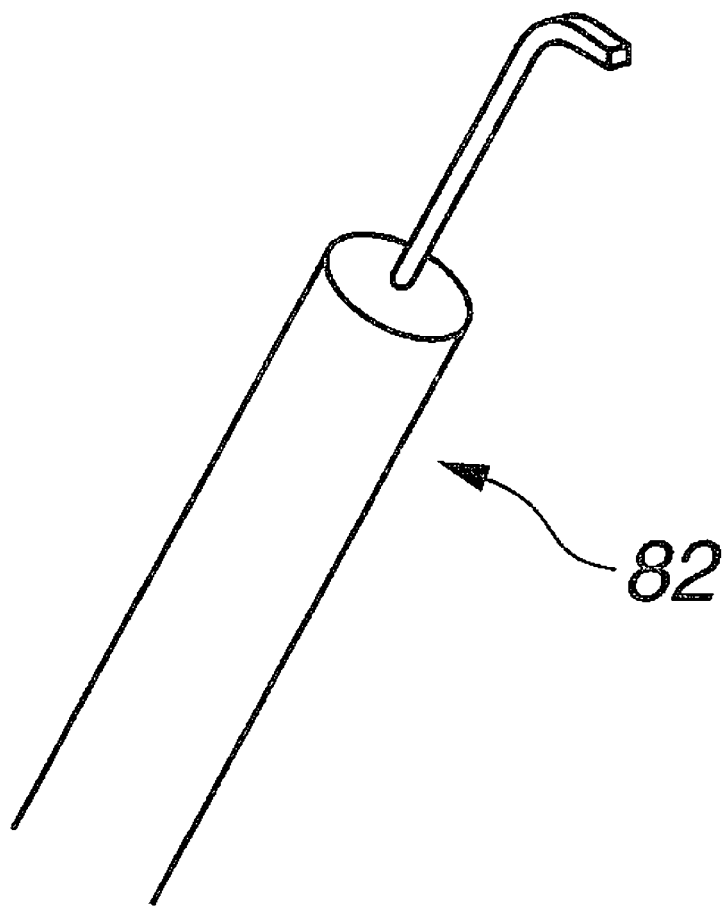
FIG. 15 is a diagram showing a hook knife as a treatment instrument not having a joint usable in the present invention.

For example, the present invention can also be applied to a treatment instrument such as an IT knife 81 shown in FIG. 14 or a treatment instrument called a hook knife 82 having a hook shape as shown in FIG. 15.

For example, when the IT knife 81 rotationally symmetrical with respect to an axis direction is inserted into the channel 5*a* of the endoscope 4 according to the first embodiment and used, the information collecting section 33 collects, for example, a detection signal of a position by the sensor section 45 shown in FIG. 2. Information concerning a direction in which the IT knife 81 is projected from a distal end opening is also necessary. However, usually, the information can be regarded as information that does not temporally change.

In this case, since the treatment instrument does not have a joint, detection of a sensor for detecting, when a treatment instrument has a joint, a change in a posture of the treatment instrument due to rotation of the joint is unnecessary.

In the case of the hook knife 82, since the hook knife 82 does not have a rotationally symmetrical shape, for example, when the hook knife 82 is applied to the first embodiment in the same manner as the IT knife 81, the information collecting section 33 collects detection signal of a position and a rotation angle by the sensor section 45 shown in FIG. 2. Information concerning a direction is also necessary, although the information does not temporally change.

Even the treatment instrument not having a joint may be configured to detect, when the treatment instrument has flexibility, plural positions on a distal end side in order to improve detection accuracy and detect a posture generally on the distal end side (e.g., a posture equivalent to a shape deformed from a straight state).

In the embodiments explained above, for example, the first embodiment, the sensors 44 and 45 different from the sensors that detect postures of the treatment instruments are used for detection of advance and retract and a direction of the treatment instruments. The present invention is not limited to this. All kinds of information concerning a position, a posture, advance and retract, and a direction may be detected by, for example, the operation mechanisms 40*a* and 40*b* section. Such a configuration example is shown in FIG. 16.

Figure 16:
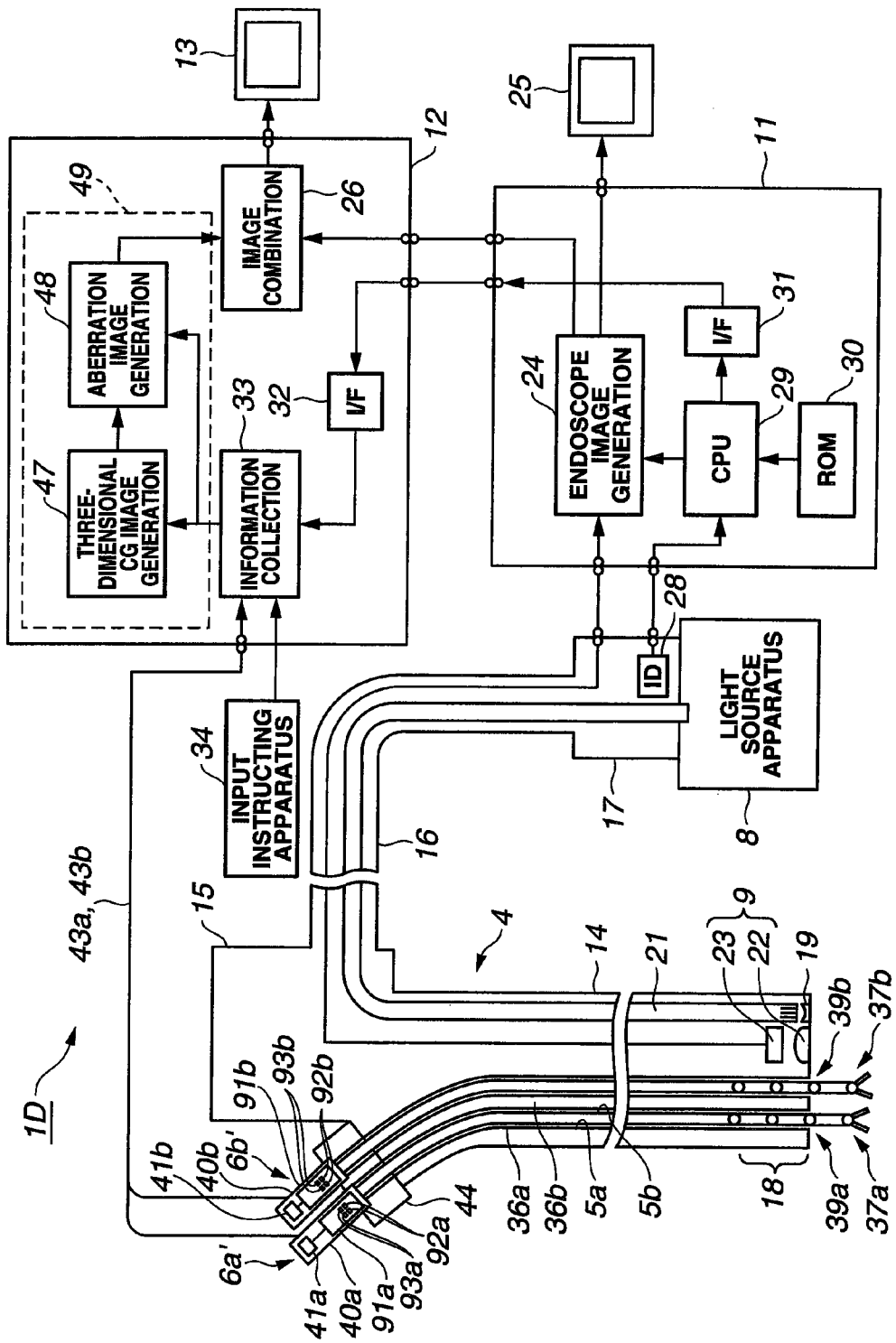
FIG. 16 is an overall diagram of an endoscope system corresponding to a modification of the first embodiment.

FIG. 16 shows an overall configuration of an endoscope system 1D corresponding to a modification of, for example, the first embodiment. In the first embodiment, the configuration example in which the sensors that detect postures of the multi joint treatment instruments 6*a* and 6*b* are provided on the inside of the multi joint treatment instruments 6*a* and 6*b* themselves, specifically, in the joint sections is explained.

On the other hand, in multi joint treatment instruments 6*a*' and 6*b*' in the endoscope system 1D, rotation (rotational movement), movement, and the like of joints are performed by plural motors 92*a* and 92*b* configuring driving sections 91*a* and 91*b* in the operation mechanisms 40*a* and 40*b* provided on an operator's side.

In this case, the plural motors 92*a* and 92*b* are provided according to the number of joints (when there is no joint, as explained below, a motor that moves in a longitudinal direction of the treatment instruments and a motor that rotates around a longitudinal axis are provided.)

Driving force by each motor 92*i* (i=a and b) is transmitted via a not-shown wire inserted through a shaft portion 36*i* to drive the joints.

In each motor 92*i*, a sensor 93*i* such as an encoder that detects a driving amount such as a rotation amount of the motor 92*i* is provided. A rotation angle of each joint is detected by each sensor 93*i*.

As the motor 92*i* in a driving section 91*i*, a motor that not only rotates joints of the multi joint treatment instrument 6*i*' but also, for example, moves a rear end of the multi joint treatment instrument 6*i*' in a longitudinal direction thereof and a motor that rotates around a longitudinal axis are also incorporated. Driving amounts of the motors are also detected by the sensor 93*i* corresponding thereto.

A detection signal detected by each sensor 93*i* is outputted, for example, from the control section 41*i* to the information collecting section 33 via a cable 43*i*. The information collecting section 33 collects information concerning portions of the multi joint treatment instrument 6*i*'. Therefore, in the endoscope system 1D, the treatment instrument holder 44 and the sensor section 45 in the first embodiment are not provided.

The control section 411 performs control for driving each motor 92*i* of the driving section 911 according to instruction operation by a user such as a surgeon. A detection signal of the sensor 93*i* is also inputted to the control section 91*i*. The control section 91*i* controls a driving amount of the motor 92*i* corresponding thereto by a value corresponding to the instruction operation by the user. Otherwise, the control section 411 has a configuration same as that in the first embodiment.

In this way, in the endoscope system 1D, all kinds of information concerning positions, postures, advance and retract, and directions of the portions of the multi-joint treatment instruments 6*a*' and 6*b*' are detected by, for example, the operation mechanisms 40*a* and 40*b* section.

The endoscope system 1D has actions and effects substantially the same as those in the first embodiment. In the endoscope system 1D, since the driving section 91*i* is provided on the operator's side, the multi joint treatment instrument 6*i*' can be easily reduced in diameter. In other words, since a motor and a sensor do not have to be provided in a joint portion, it is easy to reduce the multi joint treatment instrument 6*i* in diameter. The endoscope system 1D can also be applied to an endoscope in which an inner diameter of the channel 5*i* is small.

The endoscope system 1D can also be applied to a treatment instrument not having a joint. An embodiment and the like configured by, for example, partially combining the embodiments and the like explained above also belong to the present invention.

What is claimed is:

1. A medical apparatus system comprising:
   a medical apparatus including an observing section having an objective lens having an observation field of view;
   an image generating section configured to generate a first image of an inside of the observation field of view obtained from the observing section;
   a treatment instrument used together with the medical apparatus, at least a proximal end side of the treatment instrument being arranged on an outside of the observation field of view of the observing section;
   an information collecting section that collects information including at least a position and direction on a distal end side of the treatment instrument;
   an outside-of-observation-field-of-view computer graphic image generating section configured to generate a computer graphic image of the treatment instrument on at least the outside of the observation field of view using the information collected by the information collecting section;
   an outside-of-observation-field-of-view distortion setting section that sets virtual distortion for the computer graphic image of the treatment instrument on the outside of the observation field of view on the basis of information on a characteristic of distortion of the objective lens;
   an outside-of-observation-field-of-view distorted image generating section that generates at least a three-dimensional or two-dimensional distorted image as a second image obtained by virtually distorting the computer graphic image of the treatment instrument on the outside of the observation field of view on the basis of the information collected by the information collecting section and the virtual distortion set by the outside-of-observation-field-of-view distortion setting section; and
   an image combining section configured to generate, when the distal end side of the treatment instrument is captured on the inside of the observation field of view, a combined image which includes the first image of the treatment instrument on the inside of the observation field of view and the second image obtained by distorting the treatment instrument on the outside of the observation field of view, and in which the first image and the second image coincide with each other in a boundary of the observation field of view.

2. The medical apparatus system according to claim 1, wherein the treatment instrument is adapted to be inserted through a channel provided in the medical apparatus.

3. The medical apparatus system according to claim 2, further comprising:
   a rotatable joint provided to the distal end side of the treatment instrument; and
   a sensor that detects postures including rotation of the joint on the distal end side of the treatment instrument,
   wherein the information collecting section includes
      a first information collecting section that collects first information that does not temporally change, the first information including relative position information among a distal end opening of the channel as a reference position, a center position of the objective lens, and an observation field of view direction, and information on a direction in which the treatment instrument is projected from the distal end opening, and
      a second information collecting section that repeatedly collects posture information on the distal end side of the treatment instrument from a detection signal of the sensor.

4. The medical apparatus system according to claim 2, wherein the treatment instrument includes a joint that rotationally moves.

5. The medical apparatus system according to claim 1, wherein the treatment instrument is arranged so as to be used separately from the medical apparatus.

6. The medical apparatus system according to claim 2, wherein the information collecting section collects information concerning a position and a direction on the distal end side of the treatment instrument with respect to a position of the observing section.

7. The medical apparatus system according to claim 2, wherein the medical apparatus includes an endoscope in which the observing section including the objective lens is provided at a distal end portion of an elongated insertion portion.

8. The medical apparatus system according to claim 2, wherein the treatment instrument includes a driving section that is provided on the distal end side of the treatment instrument and electrically drives a joint.

9. The medical apparatus system according to claim 2, wherein the treatment instrument has peculiar identification information, and the information collecting section outputs, referring to the identification information, information on the distal end side of the treatment instrument used together with the medical apparatus to the outside-of-observation-field-of-view distorted image generating section.

10. The medical apparatus system according to claim 5, wherein the treatment instrument includes a joint that rotationally moves.

11. The medical apparatus system according to claim 5, wherein the treatment instrument includes a driving section that is provided on the distal end side of the treatment instrument and electrically drives a joint.

12. The medical apparatus system according to claim 1, wherein the outside-of-observation-field-of-view distortion setting section includes a storing section having stored therein information concerning virtual distortion on the outside of the observation field of view corresponding to the distortion of the objective lens provided in each of plural medical apparatuses.

13. The medical apparatus system according to claim 12, wherein the medical apparatus has peculiar identification information, and the outside-of-observation-field-of-view distortion setting section reads out information concerning virtual distortion corresponding to the identification information from the storing section and sets the virtual distortion on the outside of the observation field of view of the objective lens.

14. The medical apparatus system according to claim 1, wherein the medical apparatus has peculiar identification information, and the outside-of-observation-field-of-view distortion setting section automatically sets, on the basis of the identification information, virtual distortion on the outside of the observation field of view corresponding to the distortion of the objective lens provided in the medical apparatus.

15. The medical apparatus system according to claim 1, wherein the information collecting section collects information concerning a position and a direction on the distal end side of the treatment instrument with respect to a position of the observing section.

16. The medical apparatus system according to claim 1, further comprising a display apparatus that displays the combined image generated by the image combining section.

17. The medical apparatus system according to claim 1, wherein the outside-of-observation-field-of-view computer graphic image generating section generates a three-dimensional computer graphic image on the outside of the observation field of view as the computer graphic image; and the outside-of-observation-field-of-view distorted image generating section includes a two-dimensional computer graphic distorted image generating section that virtually distorts the three-dimensional computer graphic image and generates a two-dimensional computer graphic distorted image as the two-dimensional distorted image viewed from an observation field of view direction of the objective lens.

18. The medical apparatus system according to claim 1, wherein the medical apparatus includes an endoscope in which the observing section including the objective lens is provided at a distal end portion of an elongated insertion portion.

19. The medical apparatus system according to claim 1, wherein the medical apparatus includes a guide tube that is used separately from the medical apparatus and through which the treatment instrument can be inserted.

20. The medical apparatus system according to claim 1, wherein the treatment instrument includes a sensor that detects at least a position on the distal end side of the treatment instrument.

21. The medical apparatus system according to claim 1, wherein the outside-of-observation-field-of-view treatment instrument has peculiar identification information, and the distorted image generating section generates, on the basis of the identification information, a distorted image on the outside of the observation field of view on the distal end side of the treatment instrument corresponding to the identification information.

22. The medical apparatus system according to claim 1, wherein the outside-of-observation-field-of-view distortion setting section sets the virtual distortion using a value in a boundary with the outside of the observation field of view on the inside of the observation field of view in the distortion of the objective lens and information concerning a tilt of a tangent in the boundary.

23. The medical apparatus system according to claim 1, further comprising:
a rotatable joint provided to the distal end side of the treatment instrument; and
a sensor that detects postures including rotation of the joint on the distal end side of the treatment instrument,
wherein the information collecting section includes an observing section information collecting section that collects information on the observing section, and a posture information collecting section that repeatedly collects posture information on the distal end side of the treatment instrument from a detection signal of the sensor.

* * * * *